(12) United States Patent
Min et al.

(10) Patent No.: US 11,864,553 B2
(45) Date of Patent: Jan. 9, 2024

(54) METHODS AND SYSTEMS FOR PROVIDING RED BLOOD CELL PRODUCTS WITH REDUCED PLASMA

(75) Inventors: Kyungyoon Min, Kildeer, IL (US); Katherine Radwanski, Des Plaines, IL (US)

(73) Assignee: Fenwal, Inc., Lake Zurich, IL (US)

( * ) Notice: Subject to any disclaimer, the term of this patent is extended or adjusted under 35 U.S.C. 154(b) by 188 days.

(21) Appl. No.: 13/502,934

(22) PCT Filed: Sep. 23, 2010

(86) PCT No.: PCT/US2010/050036
§ 371 (c)(1),
(2), (4) Date: Apr. 19, 2012

(87) PCT Pub. No.: WO2011/049709
PCT Pub. Date: Apr. 28, 2011

(65) Prior Publication Data
US 2012/0225419 A1   Sep. 6, 2012

Related U.S. Application Data

(60) Provisional application No. 61/254,550, filed on Oct. 23, 2009.

(51) Int. Cl.
*A01N 1/02* (2006.01)
*A61M 1/36* (2006.01)
(Continued)

(52) U.S. Cl.
CPC ......... *A01N 1/0226* (2013.01); *A01N 1/0273* (2013.01); *A61M 1/0209* (2013.01);
(Continued)

(58) Field of Classification Search
None
See application file for complete search history.

(56) References Cited

U.S. PATENT DOCUMENTS 4,267,269 A   5/1981   Grode et al.
4,356,172 A   10/1982  Nakao et al.
(Continued)

FOREIGN PATENT DOCUMENTS

DE   4002693   3/1991
EP   0044864   8/1981
(Continued)

OTHER PUBLICATIONS

Cassady, Plasma Volume Studies in Low Birth Weight Infant 1966, Pediatrics, 38(6): 1020-1027 (Year: 1966).*
(Continued)

*Primary Examiner* — Sharmila G Landau
*Assistant Examiner* — Stephanie A McNeil
(74) *Attorney, Agent, or Firm* — Cook Alex Ltd.

(57) ABSTRACT

Methods and systems for processing and conditioning red blood cells are disclosed. The methods and systems may be used to make a readily transfusible red blood cell product with reduced plasma. In general, the plasma content of the supernatant of the red blood cell product is no greater than about 15%. The red blood cell products are prepared using the disclosed methods and systems remain transfusible for up to 42 days.

18 Claims, 5 Drawing Sheets

(51) Int. Cl.
*A61M 1/02* (2006.01)
*A61M 1/30* (2006.01)
*B01D 61/28* (2006.01)
*B01D 61/32* (2006.01)

(52) U.S. Cl.
CPC ............ *A61M 1/0236* (2014.02); *A61M 1/30* (2013.01); *A61M 1/302* (2014.02); *A61M 1/303* (2014.02); *A61M 1/308* (2014.02); *A61M 1/3693* (2013.01); *A61M 1/3696* (2014.02); *B01D 61/28* (2013.01); *B01D 61/32* (2013.01); *A61M 1/362265* (2022.05); *A61M 2202/0429* (2013.01)

(56) References Cited

U.S. PATENT DOCUMENTS

| | | |
|---|---|---|
| 4,572,899 A | 2/1986 | Walker et al. |
| 4,585,735 A | 4/1986 | Meryman et al. |
| 4,880,786 A | 11/1989 | Sasakawa et al. |
| 4,961,928 A | 10/1990 | Holme et al. |
| 4,980,277 A | 12/1990 | Junnila et al. |
| 5,147,776 A | 9/1992 | Koerner, Jr. |
| 5,248,506 A | 9/1993 | Holme et al. |
| 5,250,303 A * | 10/1993 | Meryman et al. ............ 424/533 |
| 5,288,605 A | 2/1994 | Lin et al. |
| 5,364,756 A | 11/1994 | Livesey et al. |
| 5,387,187 A | 2/1995 | Fell et al. |
| 5,405,742 A | 4/1995 | Taylor |
| 5,439,882 A | 8/1995 | Feola et al. |
| 5,445,629 A | 8/1995 | Debrauwere et al. |
| 5,446,030 A | 8/1995 | Weisz et al. |
| 5,459,030 A | 10/1995 | Lin et al. |
| 5,480,773 A | 1/1996 | Ogata et al. |
| 5,494,590 A | 2/1996 | Smith |
| 5,496,821 A | 3/1996 | Arduino |
| 5,554,527 A | 9/1996 | Fickenscher |
| 5,601,972 A | 2/1997 | Meryman |
| 5,624,794 A | 4/1997 | Bitensky et al. |
| 5,629,145 A | 5/1997 | Meryman |
| 5,674,741 A | 10/1997 | Watanabe et al. |
| 5,769,839 A | 6/1998 | Carmen et al. |
| 5,783,093 A * | 7/1998 | Holme ............ 210/767 |
| 5,789,151 A | 8/1998 | Bitensky et al. |
| 5,827,643 A | 10/1998 | Conrad et al. |
| 5,840,252 A | 11/1998 | Giertych |
| 5,888,824 A | 3/1999 | Isogowa et al. |
| 5,899,874 A | 5/1999 | Jonsson |
| 5,906,915 A | 5/1999 | Payrat et al. |
| 5,908,742 A | 6/1999 | Lin |
| 6,039,711 A | 3/2000 | Headley et al. |
| 6,068,970 A | 5/2000 | Hosono et al. |
| 6,150,085 A | 11/2000 | Hess et al. |
| 6,251,580 B1 | 6/2001 | Lin et al. |
| 6,277,556 B1 | 8/2001 | Grode et al. |
| 6,348,156 B1 | 2/2002 | Vishnoi et al. |
| 6,440,372 B1 * | 8/2002 | Pages ............ 422/534 |
| 6,447,987 B1 | 9/2002 | Hess et al. |
| 6,527,957 B1 | 3/2003 | Deniega et al. |
| 6,548,241 B1 | 4/2003 | McBurney et al. |
| 6,566,046 B2 | 5/2003 | Lin et al. |
| 6,579,672 B1 | 6/2003 | Granger et al. |
| 6,652,475 B1 | 11/2003 | Sahines et al. |
| 6,811,778 B2 | 11/2004 | Page et al. |
| 6,857,191 B2 | 2/2005 | Whited |
| 6,866,992 B2 | 3/2005 | Lin et al. |
| 6,936,413 B1 | 8/2005 | Bischof et al. |
| 7,011,761 B2 | 3/2006 | Muller |
| 7,087,177 B2 | 8/2006 | Min et al. |
| 7,156,240 B2 | 1/2007 | Oishi et al. |
| 7,264,608 B2 | 9/2007 | Bischof et al. |
| 7,267,817 B2 | 9/2007 | Page et al. |
| 7,297,272 B2 | 11/2007 | Min et al. |
| 7,332,125 B2 | 2/2008 | Cianci et al. |
| 7,531,098 B2 | 5/2009 | Robinson et al. |

| | | | |
|---|---|---|---|
| 2001/0031499 A1 * | 10/2001 | McHale ............ 435/461 |
| 2001/0049089 A1 | 12/2001 | Dottori et al. |
| 2002/0128583 A1 * | 9/2002 | Min et al. ............ 604/6.01 |
| 2002/0131958 A1 | 9/2002 | Chapman et al. |
| 2002/0146400 A1 | 10/2002 | Cincotta |
| 2002/0164795 A1 | 11/2002 | Gen |
| 2002/0177116 A1 | 11/2002 | Wiggins et al. |
| 2003/0113704 A1 | 6/2003 | Stassinopoulos |
| 2003/0113707 A1 * | 6/2003 | Gawryl et al. ............ 435/2 |
| 2003/0124504 A1 | 7/2003 | Bitensky et al. |
| 2003/0148256 A1 | 8/2003 | Payrat et al. |
| 2003/0153074 A1 | 8/2003 | Bitensky et al. |
| 2004/0029096 A1 | 2/2004 | Steen |
| 2004/0043374 A1 | 3/2004 | DePablo et al. |
| 2004/0106094 A1 | 6/2004 | Payrat et al. |
| 2004/0132207 A1 | 7/2004 | Arima et al. |
| 2004/0137417 A1 | 7/2004 | Ryan |
| 2005/0031596 A1 | 2/2005 | Crowe et al. |
| 2005/0053516 A1 | 3/2005 | Whitaker et al. |
| 2005/0064381 A1 | 3/2005 | Lucas et al. |
| 2005/0074743 A1 | 4/2005 | Purmal et al. |
| 2005/0137516 A1 | 6/2005 | Min et al. |
| 2005/0137517 A1 | 6/2005 | Blickham et al. |
| 2005/0208462 A1 | 9/2005 | Bitensky et al. |
| 2005/0233302 A1 | 10/2005 | Hess et al. |
| 2005/0256443 A1 | 11/2005 | Bischof et al. |
| 2005/0277108 A1 | 12/2005 | Bitensky et al. |
| 2006/0127375 A1 | 6/2006 | Livesey |
| 2006/0226090 A1 | 10/2006 | Robinson et al. |
| 2006/0275271 A1 | 12/2006 | Chow |
| 2006/0292544 A1 | 12/2006 | Hassanein et al. |
| 2007/0020607 A1 | 1/2007 | Meryman |
| 2007/0048726 A1 | 3/2007 | Baust et al. |
| 2007/0105220 A1 | 5/2007 | Crowe et al. |
| 2007/0178168 A1 | 8/2007 | Ho et al. |
| 2007/0178434 A1 | 8/2007 | Natan et al. |
| 2007/0190636 A1 | 8/2007 | Hassanein et al. |
| 2007/0298406 A1 | 12/2007 | Pena et al. |
| 2008/0050275 A1 | 2/2008 | Bischof et al. |
| 2008/0176209 A1 | 7/2008 | Muller et al. |
| 2008/0233554 A1 | 9/2008 | Sehgal et al. |
| 2009/0239208 A1 * | 9/2009 | Mayaudon et al. ............ 435/2 |

FOREIGN PATENT DOCUMENTS

| | | |
|---|---|---|
| EP | 0301250 A1 | 1/1989 |
| EP | 0367271 A1 | 9/1990 |
| EP | 0875756 A2 | 11/1998 |
| WO | WO8803027 A1 | 5/1988 |
| WO | WO9214360 A1 | 9/1992 |
| WO | WO9416099 A1 | 7/1994 |
| WO | WO96029864 A1 | 10/1996 |
| WO | WO9716967 A1 | 5/1997 |
| WO | WO02023988 A1 | 3/2002 |
| WO | WO04105483 A1 | 12/2004 |
| WO | WO06088455 A1 | 8/2006 |
| WO | WO07054160 A2 | 5/2007 |
| WO | WO07082916 A1 | 7/2007 |
| WO | WO08037481 A2 | 4/2008 |
| WO | WO08089337 A1 | 7/2008 |
| WO | WO08107724 A2 | 9/2008 |
| WO | WO08113017 A2 | 9/2008 |

OTHER PUBLICATIONS

Hogman et al., Sep. 2006, Storage of Red Blood Cells with Improved Maintenance of 2, 3 Biphosphoglycerate, Transfusion, vol. 46, pp. 1543-1552.
Heaton, 1992, Evaluation of Posttransfusion Recovery and Survival of Transfused Red Cells, Transfusion Medicine Reviews, vol. 6, pp. 153-169.
Hess et al, 2002, Storage of Red Blood Cells; New Approaches, Transfusion Medicine Reviews, vol. 16, pp. 283-295.
Hogman et al., 2002, Improved Maintenance of 2,3-DPG and ATP in RBCs Stored in a Modified Additive Solution, Transfusion, vol. 42, pp. 824-829.
Tinmouth et al., 2001, The Clinical Consequences of the Red Cell Storage Lesion, Transfusion Medicine Reviews, vol. 15, pp. 91-107.

(56) References Cited

OTHER PUBLICATIONS

Hogman et al., 1999, Storage Parameters Affecting Red Blood Cell Survival and Function After Transfusion, Transfusion Medicine Reviews, vol. 13, pp. 275-296.
Hess et al., The Effect of Two Additive Solutions on the Posthaw Storage of RBCS, Transfusion, Jul. 2001, pp. 923-927, vol. 41.
Hess et al., Twelve-week RBC Storage, Transfusion, Jul. 2003, pp. 867-872, vol. 43.
Hogman et al., "Clinical usefullness of red cells preserved in protein-poor mediums", New England Journal of Medicine, 1978, vol. 229 (25), pp. 1377-1382.
Hogman et al., "Storage of whole blood before separation: the effect of temperature on red cell 2, 3 DPG and the accumulation of lactate", Transfusion, 1999, vol. 39 (5) pp. 492-497.
D. Mazor, A. Dvilansky and N. Meyerstein; Prolonged Storage of Red Cells: The Effect of pH, Adenine and Phosphate; Vox Sang 1994; 66:264-269; Hemotology Service and the Dr. Joseph Kaufmann Hemotology Laboratory, Ben Gurion University of the Negev, Beer-Sheva, Israel.
John R. Hess, Neeta Rugg; Jenny K. Gormas, Amy D. Knapp, Heather R. Hill, Cynthia K. Oliver, Lloyd E. Lippert, Edward B. Silberstein and Tibor J. Greenwalt; RBC Storage for 11 Weeks; Transfusion 1586-1590; vol. 41, Dec. 2001; Blood Components XP009115151.
WebMD, Phosphate in Blood, last viewed on Nov. 15, 2011 at http://www.webmd.com/a-to-z-guides/phosphate-in-blood.
E. Beutler and W. Kuhl; Volume Control of Erythrocytes During Storage, The Role of Mannitol; pp. 353-357; XP-000909765; Department of Basic and Clinical Research, Research Institute of Scripps Clinic, LaJolla, California (1988).
European Search Report and Annex for EP Application 09004074, dated Feb. 26, 2010; pp. 1-3; Munich, Germany.
Hess et al.,"Alkaline CPD and the preservation of RCB 2,3-DPG", Transfusion, 2002, vol. 42, pp. 747-752.
Bohmer et al., "The effect of stress upon hydrolysis adenine nucleotides in blood serum of rats", Pharmacoloy, Biochemistry and Behavior, (2003) vol. 75, pp. 467-471.
Graefe, et al., "Sensitive and Specific Photometric Determination of Mannitol in Human Serum", Clinic Chem lab Med., (2003), vol. 41(8), pp. 1049-1055.
Jacobs, et al., Determination of Citric Acid in Serum and urine Using Br82, Journal of Nuclear Medicine, (1964), vol. 5, pp. 297-301.
MedlinePlus, Glucose test-blood, last viewed on Nov. 15, 2011 at http://www.nlm.nih.gov/medlineplus/ency/article/003482.htm.
Common Laboratory (LAB) Values—ABGs—Arterial blood gases, last viewed on Nov. 15, 2011 at http://www.globalrph.com/abg_analysis.htm.
Hess, J.R., "An update on solutions for red cell storage", Vox Sanguinis, (2006) vol. 91 pp. 13-19.
Pietersz, et al., "Platelet Concentrates Stored in Plasma for 72 hours at 22 C Prepared from Buffycoats of Citrate-Phosphate-Dextrose Blood Collected in a Quadruple-Bag Saline-Adenine-Glucose-Mannitol System", Vox Sang., (1985), vol. 49, pp. 81-85.
Extended European Search Report and Office Action received from the European Patent Office for EP Application No. 09004074.2 dated Mar. 5, 2010.
Notice of Transmittal of International Search Report & Written Opinion received from the International Searching Authority for PCT/US10/50036 dated Jan. 21, 2011.
EP Communication dated May 29, 2012 for EP Application No. 12000538 with European Search Report and Annex dated May 21, 2012.
Notification of Transmittal of International Preliminary Report on Patentability for PCT/US2010/050036 dated May 3, 2012.
Supplementary European Search Report and Annex for EP Application 10825379, dated Mar. 14, 2013.
Pearl, Toy, et al., Transfusion-related Acute Lung Injury: Definition and Review, Critical Care Medicine, Apr. 1, 2005, pp. 721-726, vol. 33, No. 4.
Biffl, Walter L. M.D., et al., Plasma from Aged Stored Red Blood Cells Delays Neutrophil Apoptosis and Primes for Cytotoxicity: Abrogration by Poststorage Washing but Not Prestorage Leukoreduction, Journal of Trauma-Injury Infection and Critical Care, Mar. 1, 2001, pp. 1-1, XP55055440, retrieved from the Internet: URL:http://journals.lww.com/jtrauma/pages/articleviewer.aspx?year=2001&issue=03000&article=00005&type=abstract [retrieved on Mar. 6, 2013.].
Kelher, M.R., et al., Plasma from Stored Packed Red Blood Cells and MHC Class I Antibodies Cause Acute Lung Injury In a 2-event In Vivo Rat Model, Blood, Feb. 26, 2009, pp. 2079-2087, vol. 113, No. 9.
Silbert, J.A., The Storage of Washed Human Erythrocytes In a Protein-Free Medium, Transfusion, Jan. 1, 1983, pp. 8-10.

* cited by examiner

METHODS AND SYSTEMS FOR PROVIDING RED BLOOD CELL PRODUCTS WITH REDUCED PLASMA

This is a National Stage of PCT Application No. PCT/US2010/050036, which was filed on Sep. 23, 2010, which claims the benefit of U.S. Provisional Patent Application Ser. No. 61/254,550, filed Oct. 23, 2009, which applications are incorporated by reference in their entireties.

TECHNICAL FIELD

The subject matter of the disclosure that follows is generally directed to methods for providing readily transfusible, red blood cells with minimal plasma, to red blood cell products provided by such methods, and to systems for providing the same. More particularly, the disclosure that follows relates to methods and systems for providing readily transfusible, red blood cell compositions or products that include a red blood cell portion and a supernatant portion wherein the supernatant portion includes a reduced and selected volume of plasma (as a percentage of the supernatant volume).

BACKGROUND

The administration of blood and/or blood components is common in the treatment of patients suffering from disease or blood loss. Rather than infuse whole blood, it is more typical that individual components be administered to the patient in need. For example, administration (infusion) of platelets is often prescribed for cancer patients whose ability to make platelets has been compromised by chemotherapy. Red blood cells are typically administered to patients who have suffered a loss of blood, anemia or other disorders. Infusion of plasma may also be prescribed for therapeutic reasons and, more recently, the harvesting and administration of stem cells has received widespread interest within the medical community. Thus, it is often desirable to separate and collect a blood component, (e.g., red blood cells, platelets, plasma, stem cells) from whole blood and then treat the patient with the specific blood component. The remaining components may be returned to the donor or collected for other uses.

There are several factors to be considered in the separation, collection and storage of blood components for subsequent transfusion. For example, the presence of white blood cells (e.g., leukocytes) in a blood component collected for administration is often considered to be undesirable as such leukocytes can trigger an adverse response in the recipient-patient. As a result, blood components are often "leukoreduced" prior to transfusion. Also, the presence of certain antibodies in plasma has been correlated with the occurrence of TRALI (transfusion-related acute lung injury) in some patients receiving blood components such as red blood cells. Consequently, while plasma is present to some degree in transfusible red blood cells and platelets, it is desirable to reduce the amount of plasma in the red blood cell or platelet preparation.

Red blood cells are often stored for long periods of time prior to transfusion. In this case, the environment in which the cells are stored may have to be carefully controlled to optimize or at least maintain cell properties required for effective transfusion. For example, it is usually desirable to at least maintain adenosine triphosphate (ATP) and 2,3-diphosphoglycerate (2,3-DPG) levels and limit hemolysis during storage.

Additive solutions useful for improving the storage environment of red blood cells are disclosed, for example, in pending U.S. application Ser. No. 12/408,483 filed Mar. 20, 2009 (Mayaudon et al.), and a continuation-in-part of the '483 application which is being filed on the same day as the present application and is entitled "Red Blood Cell Storage Medium for Extended Storage" (Mayaudon et al.), which serial number has not yet been assigned but which is identified by Applicant's reference number F-6542 CIP, which applications are incorporated by reference herein in their entireties.

Other additive solutions for improving the storage environment for red blood cells (and other components) are disclosed, for example, in U.S. Pat. No. 5,250,303 (Meryman), incorporated by reference herein, which discloses solutions for the extended storage of red blood cells. The solutions disclosed therein are generally chloride-free, hypotonic solutions which provide for the long-term storage of red blood cells. According to U.S. Pat. No. 5,250,303 to Meryman, the chloride-free, effectively hypotonic solutions induce a "chloride-shift" which, in turn, leads to a rise in the intracellular pH of the red blood cells. Also, according to Meryman, the rise in intracellular pH appeared to be correlated with rise in ATP and/or 2,3 DPG and, thus, prolonged storage times.

Although, Meryman recognized the benefit of using hypotonic solutions to extended storage of red blood cells generally, Merman did not appreciate the benefits of using selected relative amounts of additive solution and plasma in the storage environment for the red cells, nor did Meryman describe systems for providing such red blood cell products.

Thus, there still exists a need for methods and systems that provide readily transfusible red blood cells whereby the red blood cell environment can be controlled and enhanced by preserving the red blood cells and reducing the potential of TRALI.

SUMMARY

In one aspect, the disclosure set forth herein relates to a method for processing red blood cells. The method includes separating a quantity of blood into concentrated red blood cells and plasma. The plasma is removed, providing an initial red blood cell concentrate. Further, substantially chloride-free additive solution is combined with the red blood cell concentrate, to provide an intermediate red blood cell product. The intermediate red blood cell product is separated into a concentrated red blood cell component and a supernatant component, which includes at least plasma and additive solution. The supernatant component is substantially removed from the intermediate red blood cell product to provide a treated red blood cell concentrate. A second portion of the substantially chloride-free additive solution may be combined with the treated red blood cell concentrate, providing a red blood cell product that includes the treated red blood cell concentrate and a supernatant component. The percentage of plasma in said supernatant is no greater than about 15%.

In another aspect, the disclosure herein also relates to a red blood cell product which includes a concentrated red blood cell portion and a supernatant portion. The supernatant portion includes a substantially chloride-free additive solution and plasma. The plasma content of the supernatant is no greater than about 15%.

In a further aspect, the disclosure herein also relates to a system for reducing the plasma content of a red blood cell preparation. The system includes a first container that has at least one resealable port. The system also has a vent line with proximal and distal ends. The vent line is in fluid communication at its proximal end with the first container. The vent line has a volume of from about 20 mls to about 50 mls. The system also includes a second container and a flow path establishing fluid communication between the first and second containers. The vent line is in fluid communication with the second container. The system also includes a flow controller which is in adjustable flow communication with the vent line and the second container.

DETAILED DESCRIPTION

The subject matter of the present disclosure relates generally to methods and systems for processing readily infusible red blood cells, systems useful for carrying out such methods and the red blood cell products obtained by such methods and systems.

Methods of processing red blood cells and/or providing a red cell product that are/is readily transfusible are explained in detail below. By "readily transfusible," it is meant that the red blood cell preparation has a sufficiently reduced volume of plasma so as to minimize the potential incidence of TRALI, retains acceptable levels of ATP and 2,3-DPG, and acceptable levels of % hemolysis after storage. In addition, "readily transfusible" also refers to a volume of the red blood cell composition or product that can be safely infused into the patient.

As noted above, the presence of antibodies in plasma is correlated with the occurrence of TRALI. Accordingly, the systems and methods disclosed herein may be effective in reducing the incidence of TRALI. Thus, the plasma content in the supernatant of the red blood cell composition or product prepared using the methods of the present disclosure is no greater than about 15%. In a further embodiment, the plasma content may typically be from about 6% to about 11% of the supernatant volume of the red blood cell composition, or product.

As noted above, the red blood cell products disclosed herein are also considered readily transfusible because ATP and 2,3-DPG levels remain sufficiently elevated after extended storage. For example, red blood cell products and compositions of the type disclosed herein maintain acceptable levels of ATP for up to 42 days of storage. Also the stored red blood cells retain more than 50% of initial 2,3-DPG levels after 28 days of storage. More preferably, the stored red blood cells retain more than 80% of initial 2,3-DPG levels after 28 days of storage. Finally, red blood cell products and compositions of the type described herein maintain acceptable levels of % hemolysis after extended storage.

The systems and methods of the present disclosure may also be used to establish or control the conditions under which red blood cell products may be stored before transfusion. Thus, the methods may be used to introduce additive solutions or reagents that may improve the storage properties of the red blood cells, thereby providing a transfusible red blood cell product.

Figure 1:
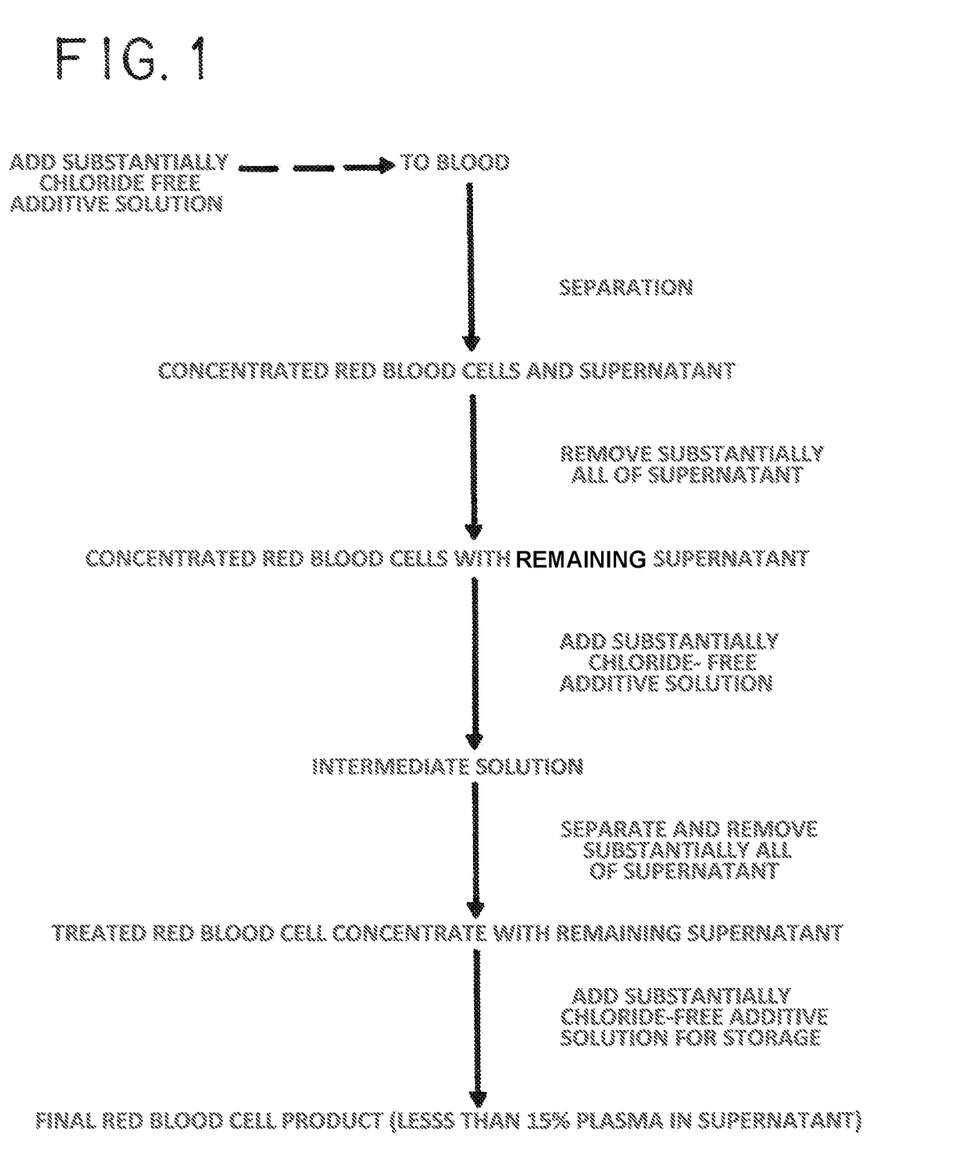
FIG. 1 is a flow chart setting forth the method of providing readily transfusible, red blood cells in accordance with the disclosure set forth herein.

In one embodiment, the method for providing readily transfusible, red cells disclosed herein (and depicted in FIG. 1) includes providing a quantity of blood, typically in a container. As used herein, the term "blood" is meant to include unfractionated and typically anticoagulated whole blood as well as a red blood cell concentrate that has been previously derived (i.e., separated) from whole blood. Thus, for example, the blood may be a packed or concentrated red blood cells (i.e., red blood cell concentrate) having a hematocrit of at least 70% and more preferably at least 80% and most preferably at least 90% or higher.

Preferably, however, the "blood" is provided as whole blood in a container which can be a blood processing, collection or storage container of the type conventionally used in so-called "manual" or "whole blood" processing, or containers such as those used in automated apheresis. With regard to automated apheresis, the container in which the separation of blood or the processing of blood components may occur may also refer to the chamber of the separation device, such as a centrifuge or spinning membrane. Non-limiting examples of these are the separation chambers used in the Alyx® separator, Amicus® separator and Autopheresis®-C separator, all made and sold by Fenwal, Inc. of Lake Zurich, Illinois Regardless of whether the "blood" is provided as unfractionated whole blood or an already separated-from-whole blood red blood cell concentrate, the blood is separated (for the first time or further separated, depending on the composition of the starting "blood") into red blood cell concentrate and plasma, including any residual anticoagulant from the initial draw.

Where the source of blood is whole blood, a typical volume of whole blood is approximately 400-500 ml. In accordance with the method described herein, the blood may be spun to preferably result in a red blood cell concentrate having a hematocrit of preferably at least 90%. Plasma and residual anticoagulant form a supernatant layer, while the volume of the red blood cell concentrate separated from the supernatant may be approximately 150-250 ml. Once the desired volume of the packed red blood cells or red blood cell concentrate has been obtained, the method of the present disclosure includes physically separating and removing substantially all of the supernatant plasma layer (with anticoagulant) from the red blood cells. Not all of the supernatant, however, is removed and therefore the initial red blood cell concentrate will typically include about 10-30 ml of remaining supernatant.

As will be described in connection with systems used for carrying out the method disclosed herein, the separated plasma may be expressed to a satellite container of an integrated processing set. Plasma may be expressed using a component extraction device such as the Optipress, available from Fenwal, Inc. of Lake Zurich, Illinois or Compomat, available from Frensius Kabi of Bad Homburg, Germany. The separated and now isolated plasma may be further processed, as necessary. The plasma may be "platelet-rich plasma" or "platelet-poor plasma" which in the case of the latter, may include a layer of buffy coat between the supernatant platelet-poor plasma layer and packed red blood cell layer.

With substantially all of the plasma (and anticoagulant) of the supernatant removed, a selected quantity or volume of additive solution is added to the initial red blood cell concentrate remaining in the initial container in which the whole blood (or other "blood") was provided, or in a separate container. The volume of additive solution added to the initial red blood cell concentrate may be anywhere between approximately 50-500 ml, with between about 100-300 mls being preferred and approximately 200 ml being most typical and preferred. The initial red blood cell concentrate that has been combined with the selected volume of additive solution is referred to herein as the "intermediate" blood cell product. The intermediate blood cell product preferably includes between approximately 150-250 mL, and more preferably approximately 200 ml of red blood cells, approximately 10-30 ml of the remaining supernatant and the added volume of additive solution as described above.

In accordance with one embodiment of the present disclosure, such intermediate red blood cell product may be further separated into a further red blood cell concentrate and a supernatant component that includes plasma, additive solution and anticoagulant. As described above, separation of the red blood cell concentrate from supernatant may be accomplished by centrifuging, by membrane separation or even by gravity.

Once the intermediate red blood cell product has been separated to provide a red cell component and a supernatant component, substantially all of the supernatant is expressed off into a satellite or other container, to provide a "treated" red blood cell concentrate. The treated red blood cell concentrate will typically include approximately 150-250 mL of red blood cells and a hematocrit of preferably greater than 80% and more preferably greater than 90%. The treated red blood cell concentrate may also include some remaining supernatant component having a volume of approximately 10-30 ml that includes plasma, additive solution and anticoagulant.

The "treated" red blood cell concentrate may then be combined with another selected (or second) amount of an additive solution of the type described above. For example, approximately 100-150 ml of additive solution may be added to the treated red blood cell concentrate, and more preferably, approximately 105-110 ml of additive may be added to the treated red blood cell concentrate to provide a final red blood cell product. Thus, upon addition of the additive solution to the treated red cell concentrate, the "final" red blood cell product or composition includes the treated red blood cell concentrate and the supernatant component made up of the residual plasma, anticoagulant and additive solution. The final and readily transfusible red blood cell product may include between approximately 150-250 ml of red blood cells, approximately 100-150 of additive solution and approximately 10-30 ml of the remaining supernatant component that includes plasma, additive solution and anticoagulant for a total volume of approximately 260-430 ml. This "final" product, which preferably will have a hematocrit of about 50-60% may then be stored until use or transfusion. In accordance with the method described herein, the percentage of plasma in the combined volume of additive (e.g. approximately 100-150 ml) and remaining supernatant component (e.g. approximately 10-30 ml) is no greater than 15%, and more preferably, may be between about 6% and 15%.

In a preferred embodiment, as mentioned above, the percentage amount of plasma as a percentage of the volume of additive solution combined with the volume of remaining supernatant component of the "final" red blood cell product is preferably no greater than about 15%. As will be described below, a supernatant component that includes no greater than 15%, provides an environment where the overall plasma volume is sufficiently low that the incidence of TRALI can be diminished and the levels of ATP and 2,3-DPG sustained such that the red blood cells are transfusible even after prolonged storage.

While the method described above contemplates more than one addition of the additive solution to arrive at the "final" product, further additions of additive solutions and removals of supernatant may be desired and required to arrive at a plasma level that is no greater than 15% of the supernatant. Alternatively, a single "wash" with an additive solution may also be sufficient. That is, a separation of "blood" into red blood cell concentrate and plasma, followed by one and only one addition of additive solution wherein the plasma makes up no greater than 15% of the supernatant is also within the scope of the invention described herein.

Figure 2:
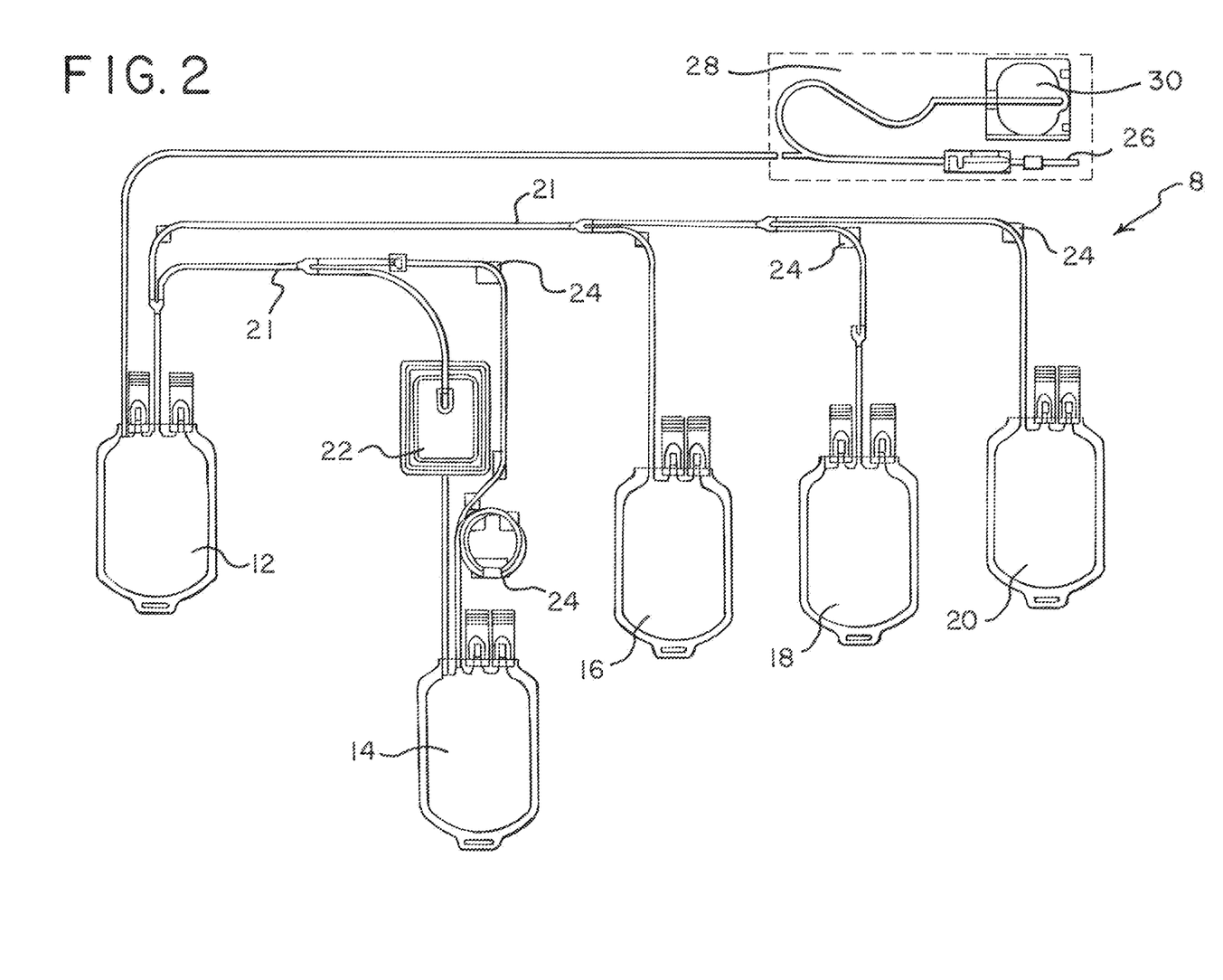
FIG. 2 is a plan view of a processing set suitable for providing red blood cell product with minimal plasma in accordance with the method described herein.

A variety of systems may be used to obtain a red blood cell product in accordance with the present disclosure. For example, FIG. 2 shows an embodiment of a system (processing set) 8 which may be employed to provide a red blood cell product according to the disclosure herein. In this embodiment, this system includes a plurality of interconnected containers in open or openable fluid communication with each other. The system or set may be closed or functionally closed without the need for sterile connection or any containers. A first bag 12 contains the blood to be processed. The containers and tubing defining the various flow paths may be made from a suitable plastic material of the type used in the medical field, such as, but not limited to polyvinyl chloride. The materials used for the containers and tubing and, thus, the entire set are/is sterilizable by, but not limited to, autoclaving.

As shown in FIG. 2, processing set 8 includes a plurality of plastic containers interconnected by tubing segments. Set 8 includes a first container 12 for holding the source of blood such as, but not limited to, whole blood to be processed in accordance with the method described herein. As will be described below, set 8 also includes satellite containers 14, 16, 18 and 20. Preferably, container 14, initially empty, will receive the final red blood cell product. A leukoreduction filter 22 may also be provided to leukoreduce the red blood cells. Containers 16 and 18 preferably contain an additive solution as described above, while container 20, also initially empty, will receive plasma separated from source blood in container 12. The container 12 is in fluid communication with each of four other bags (14, 16, 18, 20) through flow paths defined by tubing 21. Flow through processing set 8 may be controlled by flow controllers such as clamps, frangible connectors, valves or switches which are generally referenced by reference numeral 24.

Set 8 as shown in FIG. 2, also may include means for accessing the vascular system of a donor such as a needle, blunt cannula or other access member, generally referenced by numeral 26, and a sample diversion and collection subunit 28 including sample pouch 30. These features are shown for illustrative purposes only as the method described herein and recited in the appended claims does not require and is not dependent upon connection to a living donor, just as it does not require administration of the final blood product to the same donor or a patient. Although the method of the present disclosure speaks to providing readily transfusable red blood cells, the later transfusion is not necessarily required as part of the method. In short, in its broader aspects, the method of the present disclosure is directed to the processing of blood regardless of its source and/or the timing of its collection, and/or the subsequent administration of it to a patient or donor.

Thus, according to one embodiment for providing a red blood cell product, blood such as, but not limited to whole blood, in container 12. As noted above, the volume of whole blood in container 12 is typically between 400-500 mls. The blood is subjected to a separation step such as centrifugation to separate the blood into red blood cell concentrate and plasma. After centrifugation, plasma may then be manually separated from the whole blood and transferred to a second container 20. The plasma in the second container 20 may be retained for further processing. The red blood cell concentrate is retained in the first container 12 and includes about 200 ml of red cells and about 10-30 ml of plasma and anticoagulant (e.g., CPD).

After the plasma has been expressed from the container and physically separated from red blood cell concentrate (by, for example, an Optipress or other component extractor), a selected volume, approximately 200 ml, of an additive solution of the type described above may be transferred from a container 16 to container 12 containing the red blood cell concentrate to form an intermediate red blood cell product. After combining the additive solution with the red blood cell concentrate, the intermediate red blood cell product may be further processed by, for example, centrifuging the contents of at least container 12 and separating the supernatant, containing plasma and additive solution, from the red blood cell concentrate. (It will be appreciated that platelet-rich-plasma in container 20 may be simultaneously centrifuged to provide plasma and platelet concentrate). Preferably, the intermediate solution is subjected to a hard spin of at least 5,000 g for approximately 10 minutes such that the resulting red blood cell concentrate has a hematocrit of approximately 90%. As a consequence of mixing the additive solution with the red blood cell concentrate, separating the intermediate solution and expressing the supernatant, the plasma content of the red blood cell composition is reduced.

After the supernatant has been expressed or otherwise physically separated from the red blood cell concentrate, a second portion of a selected volume of an additive solution may be transferred from a container 18 to the red blood cell concentrate remaining in the first container 12, to provide, preferably, the "final" product. The red cell concentrate remains in contact with the additive solution during the period of storage and until use. Where the volume of the red blood cell concentrate is approximately 150-250 mls, an additive solution of between about 100-150 mls may be used, and wherein about 105 mls of additive solution is preferred.

In an alternative embodiment, the initial step of separating whole blood into red blood cell concentrate and plasma may be omitted so that the additive solution (container 16) may be directly added to the whole blood in container 12. This is illustrated, for example, in FIG. 1, where the addition of additive solution to whole blood is shown as a phantom (dotted) lines/arrow. In other words, whole blood in the first container 12 is combined with a selected volume of an additive solution before the separation and expression of plasma from the first container. Containers may be sized so as to allow for the combination of whole blood and additive solution which may be provided in a volume of at least approximately 100 ml, preferably greater than 100 ml and, more preferably, about 100-350 ml. After combining the additive solution with the whole blood, the combination is centrifuged to provide a red blood cell concentrate and supernatant portion. The supernatant is then expressed into the container 20, leaving a red blood cell concentrate in the container 12. A further volume of additive solution may be added to the red blood cell concentrate, as required as in the manner described above.

The method disclosed herein may also be practiced using automated apheresis devices. For example, as mentioned briefly above, the Alyx® separator, Amicus® separator and/or the Autopheresis-C separator, all made by Fenwal Inc., of Lake Zurich Illinois, USA are examples of devices that may be used to provide red blood cell products with reduced plasma in accordance with the method described herein.

Figure 3:
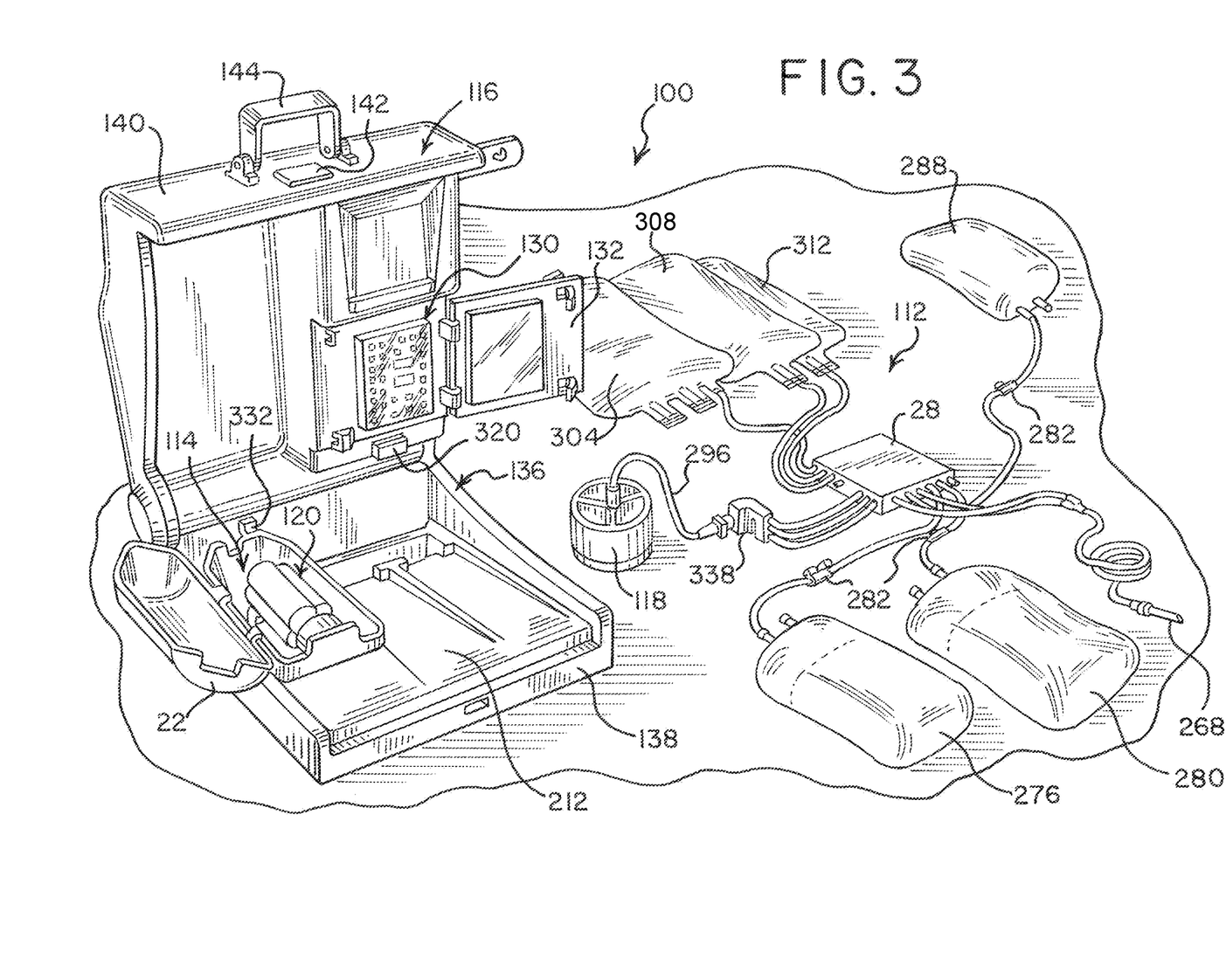
FIG. 3 is a perspective view of an apheresis system suitable for practicing the methods described herein.

In one example, FIG. 3 shows an embodiment of the Alyx® separation system that may be used to provide a red blood cell preparation according to the present disclosure. An exemplary system is described in greater detail in U.S. Pat. No. 6,348,156, which is incorporated by reference herein in its entirety. The system is also briefly described below. Examples of the Autopheresis-C® and the Amicus® separators, which may also be used to provide red cell products or concentrates of the type described herein are described in U.S. Pat. No. 5,194,145 to Schoendorfer and U.S. Pat. No. 5,547,453 to DiPerna, respectively, which are also incorporated herein by reference in their entireties.

The system 100, as shown in FIG. 3, includes three principal components. These are (i) a liquid and blood processing set 112; (ii) a blood processing device 114 that interacts with the flow set 112 to cause separation and collection of one or more blood components; and (iii) a controller 116 that governs the interaction to perform a blood processing and collection procedure selected by the operator.

The blood processing device 114 and controller 116 are intended to be durable items capable of long term use. In the illustrated and preferred embodiment, the blood processing device 114 and controller 116 are mounted inside a portable housing or case 136. The case 136 presents a compact footprint, suited for set up and operation upon a table top or other relatively small surface. The case 136 is also intended to be transported easily to a collection site.

The case 136 includes a base 138 and a hinged lid 140, which opens (as FIG. 3 shows) and closes. The lid 140 includes a latch 142, for releasably locking the lid 140 closed. The lid 140 also includes a handle 144, which the operator can grasp for transporting the case 136 when the lid 140 is closed. In use, the base 138 is intended to rest in a generally horizontal support surface.

The case 136 can be formed into a desired configuration, e.g., by molding. The case 136 is preferably made from a lightweight, yet durable, plastic material.

The flow set 112 is intended to be a sterile, single use, disposable item. Before beginning a given blood processing and collection procedure, the operator loads various components of the processing set 112 in the case 136 in association with the device 114. The controller 116 implements the procedure based upon preset protocols, taking into account other input from the operator. Upon completing the procedure, the operator removes the flow set 112 from association with the device 114. The portion of the set 112 holding the collected blood component or components are removed from the case 136 and retained for storage, transfusion, or further processing. The remainder of the set 112 is removed from the case 136 and discarded.

The processing set 112 shown in FIG. 3 includes a blood processing chamber 118 designed for use in association with a centrifuge. Accordingly, as FIG. 2 shows, the processing device 114 includes a centrifuge station 120, which receives the processing chamber 118 for use. The centrifuge station 120 comprises a compartment formed in the base 138. The centrifuge station 120 includes a door 122, which opens and closes the compartment. The door 122 opens to allow loading of the processing chamber 118. The door 122 closes to enclose the processing chamber 118 during operation.

The centrifuge station 120 rotates the processing chamber 118. When rotated, the processing chamber 118 centrifugally separates whole blood received from a donor into component parts, e.g., red blood cells, plasma, and buffy coat comprising platelets and leukocytes.

It should also be appreciated that the system 110 need not separate blood centrifugally. The system 110 can accommodate other types of blood separation devices, e.g., a membrane blood separation device.

As described in U.S. Pat. No. 6,348,156, system 100 includes a fluid pressure actuated cassette 128. Cassette 128 interacts with pneumatic actuated pump and valve station 130. The pump and valve station 130 apply positive and negative pneumatic pressure upon cassette 128 to direct flow through the system.

Figure 4:
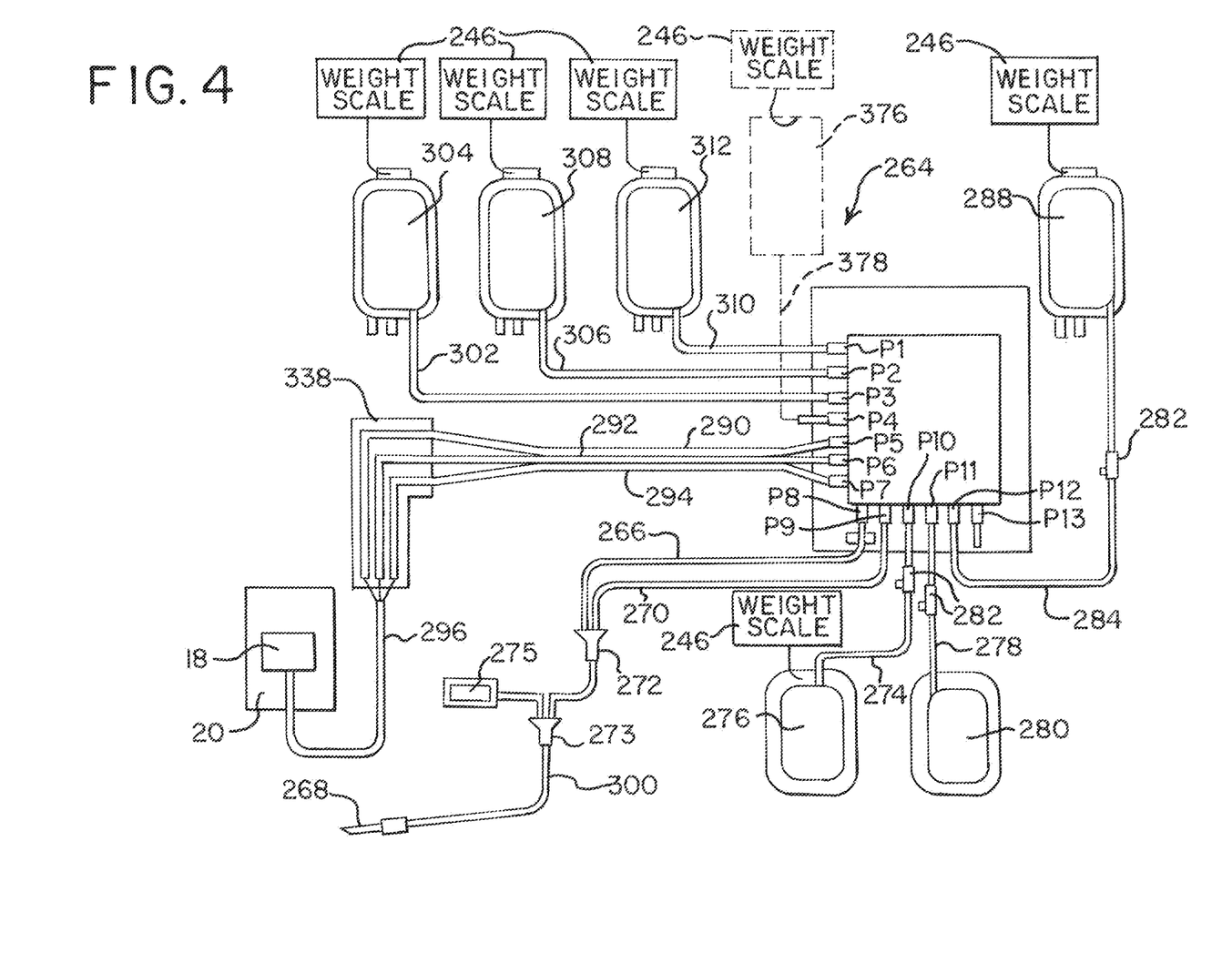
FIG. 4 is a plan view of a processing set for use with the system of FIG. 3.

FIG. 4 schematically shows a processing set 264, which, by selective programming of the blood processing circuit implemented by cassette 128, is capable of performing the blood processing method described herein. The set 264 includes a donor tube 266, which is attached (through y-connectors 272 and 273) to tubing 300 having an attached phlebotomy needle 268. The donor tube 266 is coupled to the port P8 of the cassette 128.

A container 275 for collecting an in-line sample of blood drawn through the tube 300 is also attached through the y-connector 273.

An anticoagulant tube 270 is coupled to the phlebotomy needle 268 via the y-connector 272. The anticoagulant tube 270 is coupled to cassette port P9. A container 276 holding anticoagulant is coupled via a tube 274 to the cassette port P10. The anticoagulant tube 270 carries an external, manually operated in line clamp 282 of conventional construction.

A container 280 holding a red blood cell additive solution of the type described herein is coupled via a tube 278 to the cassette port P3. The tube 278 also carries an external, manually operated in line clamp 282. A container 288 holding saline is coupled via a tube 284 to the cassette port P12.

FIG. 4 shows the fluid holding containers 276, 280, and 288 as being integrally attached during manufacture of the set 264. Alternatively, all or some of the containers 276, 280, and 288 can be supplied separate from the set 264. The containers 276, 280, and 288 may be coupled by conventional spike connectors, or the set 264 may be configured to accommodate the attachment of the separate container or containers at the time of use through a suitable sterile connection, to thereby maintain a sterile, closed blood processing environment. Alternatively, the tubes 274, 278, and 284 can carry an in-line sterilizing filter and a conventional spike connector for insertion into a container port at time of use, to thereby maintain a sterile, closed blood processing environment.

The set 264 further includes tubes 290, 292, 294, which extend to an umbilicus 296. When installed in the processing station, the umbilicus 296 links the rotating processing chamber 18 with the cassette 28 without need for rotating seals. The tubes 290, 292, and 294 are coupled, respectively, to the cassette ports P5, P6, and P7. The tube 290 conveys whole blood into the processing chamber 18. The tube 292 conveys plasma from the processing chamber 18. The tube 294 conveys red blood cells from processing chamber 18.

A plasma collection container 304 is coupled by a tube 302 to the cassette port P3. The collection container 304 is intended, in use, to serve as a reservoir for plasma during processing. A red blood cell collection container 308 is coupled by a tube 306 to the cassette port P2. The collection container 308 is intended, in use, to receive a first unit of red blood cells for storage. A whole blood reservoir 312 is coupled by a tube 310 to the cassette port P1. The collection container 312 is intended, in use, to serve as a reservoir for whole blood during processing. It can also serve to receive a second unit of red blood cells for storage.

Using an automated apheresis device of the type shown in FIGS. 3 and 4, whole blood in container 312 is introduced into processing chamber 118 where it is separated into packed red blood cells and plasma. Packed red cells flow from processing chamber 118 to red blood cell container 308. At least a portion of the red cells may be transferred from container 308 to container 312 where they are combined with an additive solution of the type described above from container 280 to provide an intermediate red blood cell product. The intermediate red blood cell product may be introduced into processing chamber 118 to separate red blood cell concentrate from "supernatant" (i.e., plasma, additive solution and an anticoagulant such as ACD). The concentrated red blood cells may be returned to container 308 where they may be combined with another volume of additive solution from container 280. The red blood cell concentrate may be combined with the additional additive before or during leukoreduction. The "final" red blood cell product may be transferred and stored in a final storage container (not shown).

As indicated above, it may not be necessary to process all of the red blood cell concentrate in container 308. The system may be programmed to deliver only a portion of the red cell concentrate to, for example, container 312, for combination with the additive solution, and for removal of supernatant such that the final red blood cell product will have a volume of plasma that is no greater than 15% of the supernatant volume in the final product. This "partial wash" reduces the time required for overall processing.

In an alternative embodiment, the system may also be programmed to deliver red blood cells and additive solution separately to the processing chamber 18 and thereby allow mixing of the cells and solution and formation of the intermediate product to occur within the chamber.

Figures 5, 6, 7:
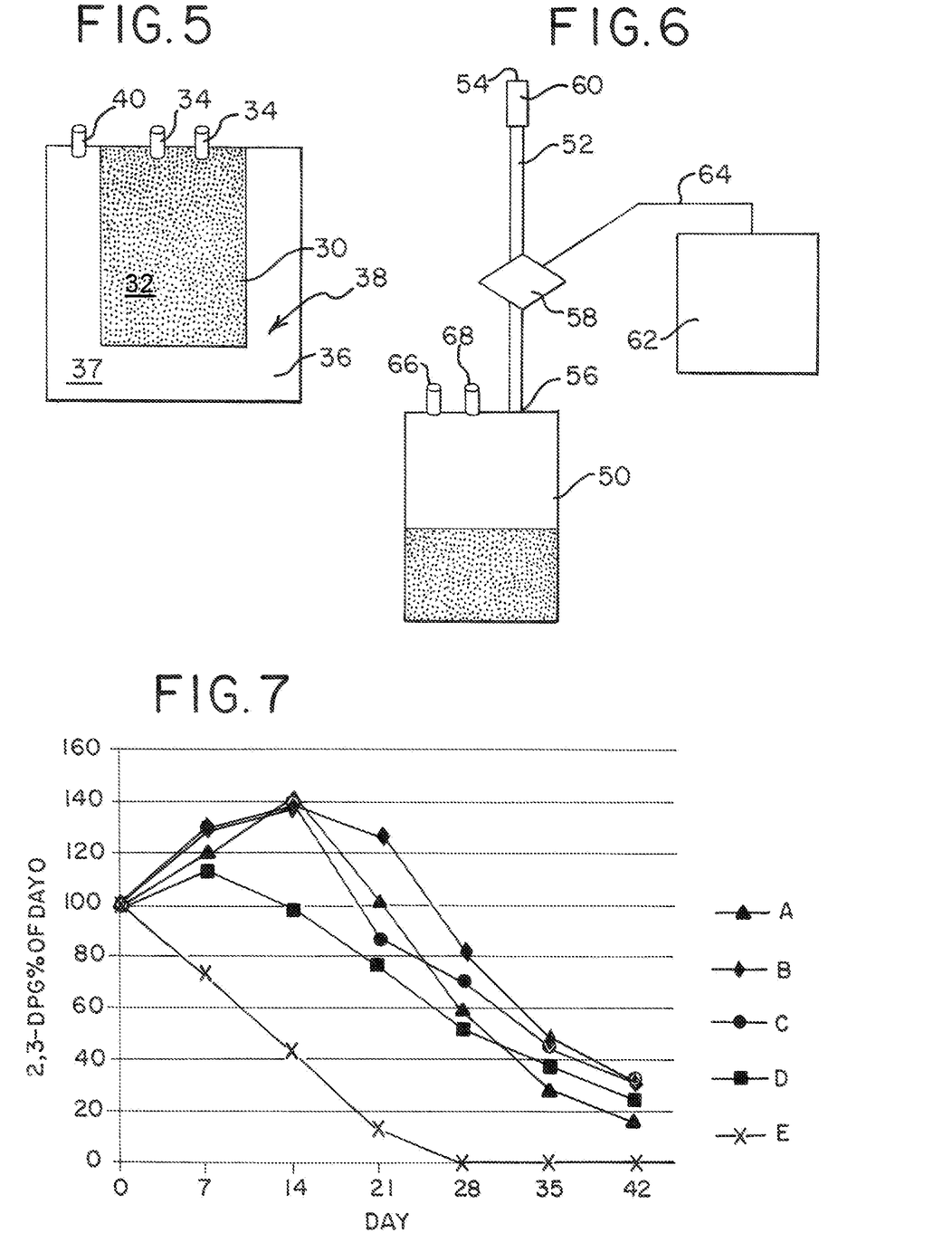
FIG. 5 is a plan view of container; system suitable for use with the method described herein.
FIG. 6 is a plan view another container suitable for use with the method described herein.
FIG. 7 is a graph showing extracellular 2,3-DPG levels during storage of red blood cell preparations made by different procedures.

FIG. 5 shows a further embodiment that may be used to provide a red blood cell product with minimal plasma in accordance with the method disclosed herein. In this embodiment, a first container 30 includes one or more walls 32 made of a porous material to, in effect, provide a porous membrane. The container may have ports 34 for accessing the interior chamber of the container. Container 30 is enclosed and housed within second container 36. The walls 37 of container 36 are non-porous and non-permeable. The volume of the second container is generally more than the volume of the first container. This container may also have ports 40 for accessing the interior of the container.

According to one embodiment, a red blood cell composition, is introduced into container 30 and an additive solution is introduced into the chamber 38 the second container 36. As a percentage of the plasma, additive solution and anticoagulant contained within the container system of FIG. 5, the volume of plasma relative to such components (other than the red blood cells—i.e. supernatant) is preferably no greater than 15%. In this example, the term "supernatant" is not used to describe a discrete and separate layer, but rather that portion of the overall composition that is not red cell concentrate. The porosity of the wall 32 of container 30 is selected such that selected components (but not the red blood cells themselves) are permitted to move, by diffusion, from one container to another. For example, molecules of the additive solution may move from the second container to the first container, thereby stabilizing the red blood cells during storage. More particularly, during storage, ions and other small molecules are able to diffuse back and forth across the porous membrane of container 30. Thus, the concentration of chloride ions and any other deleterious small molecules (cytokines, free Hb) in the red blood cells will be reduced as they diffuse across the membrane. As a further added step, the concentrated red blood cells may be pre-diluted with the additive solution. This may minimize water movement across the membrane thereby helping maintain the desired hematocrit. The red blood cells may be stored, up to 42 days. In this way, a red blood cell product that has reduced plasma content may be formed.

FIG. 6 shows a further embodiment of a system that may be used to provide a red blood cell product with minimal plasma. This embodiment includes a first container 50. The system also includes a vent line 52 that is inserted into the first container, the vent line 52 having distal end 54 and proximal end 56. The volume of the vent line is preferably from about 20 mls to about 50 mls. The vent line 52 may also include a flow control device 58 for controlling flow between containers 50 and 62 (discussed below). In some embodiments, the distal end of the vent line may be covered with or otherwise include a hydrophobic membrane 60. A second container 62 is in fluid communication with both the first container 50 and the vent line 52. In a preferred embodiment, the second container directly communicates with the vent line through tubing 64.

In this embodiment, the vent line is displayed as tubing, but in other embodiments it may be a bag or pouch.

According to one embodiment, a red blood cell composition may be introduced into the first container 50. The red blood cell composition may, for example, be whole blood. The composition may be separated by centrifugation into red blood cell concentrate, plasma and an intermediate layer of a "buffy coat" between the red blood cell concentrate layer and plasma (e.g., platelet poor). Using a conventional component extraction device, plasma may be expressed into the second container, leaving concentrated red blood cells in the first container. After the expression of plasma, a portion of red blood cells at the top of the concentrated red blood cell layer may be expressed into the vent line 52, to thereby ensure that substantially all of the plasma has been expressed from the container and thus further reducing the content of plasma of the concentrated red blood cells. In one embodiment, this portion of red blood cells is from about 20 to 50 mls per unit of whole blood which corresponds to the volume of the flow path within vent line 52. While some red blood cells may be removed to container 50, removal of substantially all of the plasma occurs.

A mechanical flow control device 58 may be used to control the flow of plasma and of red blood cells from the first container. For example, in one embodiment, a rotating cam may be used to "pinch off" the plasma or red blood cell flow paths. An operator may release a lever to allow plasma to flow into the first container. When the flow of plasma is complete, the operator closes the plasma flow path and causes the flow of red blood cells to the vent line to begin.

The vent line automatically stops filling when the vent line is full. The presence of hydrophobic membrane 62 at the distal end 54 of vent line 52 may facilitate the arrest of red blood cell flow. The operator may then seal first container 50 from the second container 62 and vent line 52 and an additive solution may be added to container 50 through ports 66 and 68 for storage. The volume of plasma as a percentage of the supernatant is preferably no greater than 15%.

According to this embodiment, an additive solution may be added to the concentrated red blood cells and the cells stored for subsequent transfusion.

Additive Solution

As mentioned above, there are many additive solutions known for the conditioning, treatment and/or preservation of red blood cells. However, solutions that are at least substantially chloride-free, nutrient-containing, having a pH that is neutral or above-neutral (e.g., preferably 7.0 or greater, and more preferably 8.0 or greater) are particularly well suited for the methods disclosed herein.

In one embodiment, in accordance with the present disclosure, the red blood cells are treated with an additive solution that is substantially chloride-free. Chloride-free additive solutions are described in co-pending application Ser. No. 12/408,483 filed Mar. 20, 2009, and a continuation-in-part of the '483 application entitled "Red Blood Cell Storage Medium for Extended Storage" (Mayaudon et al.) which is being filed on the same day as the present application, which serial number has not yet been assigned but which is identified by Applicant's reference F-6542 CIP, the contents of which applications are hereby incorporated by reference in their entireties. The compositions of such additive solutions are also described in Table 1:

TABLE 1

| Component (mmol/L) | E-Sol 2 | E-Sol 3 | E-Sol 4 | E-Sol 5 |
|---|---|---|---|---|
| Sodium Citrate dihydrate, EP | 20.8 | 31.2 | 28.4 | 25.0 |
| Sodium Phosphate dibasic, anhydrous | 16.7 | 25.0 | 22.7 | 20.4 |
| Mannitol, EP | 33.3 | 50.0 | 45.4 | 39.9 |
| Adenine, EP | 1.4 | 2.0 | 1.9 | 2.0 |
| Dextrose, monohydrate, EP | 37.8 | 56.8 | 51.6 | 111 |
|  | 150 mL | 100 mL | 110 mL | 105 mL |

Table 1 sets forth four exemplary formulations of storage solution suitable for addition to the concentrated (packed) red blood cells prepared from one unit of blood. The storage solutions are useful for the extended storage of red blood cells (e.g. approximately 42 days or greater) that have been separated from whole blood. The solutions disclosed herein are particularly useful for the extended storage of red blood cells that have been separated from whole blood that has been held for periods, such as 4 hours, 8 hours or more than 8 hours, including up to 26 hours.

As set forth in Table 1, the solution "E-Sol 2" is provided in a volume of 150 ml, "E-Sol 3" is provided in a volume of 100 ml, "E-Sol 4" is provided in a volume of 110 ml, and "E-Sol 5" is provided in a volume of 105 ml.

The storage solutions are generally applicable to the storage of red blood cells that have been manually separated from whole blood or have been separated using automated collection devices such as the Autopheresis-C® separator, the Amicus® separator and/or the Alyx® separator mentioned above.

In one embodiment, a red blood cell storage medium is provided that includes nutrients, buffers and salts. The red blood cell storage solution may be an aqueous solution which may include about 3 mM to about 90 mM sodium citrate; about 15 mM to about 40 mM sodium phosphate; about 20 mM to about 140 mM dextrose; about 20 mM to about 110 mM mannitol; and about 1 mM to about 2.5 mM adenine; the storage solution may have a pH of from about 8.0 to about 9.0. The osmolarity of the solution may be from about 200 mOsm/l to about 320 mOsm/l. The storage solution may optionally contain from about 10 mM to about 100 mM acetate. Optionally, guanosine may also be present in the storage solution from about 0.1 mM to about 2 mM. In addition, gluconate may be present from about 0 mM to about 40 mM. Optionally, a combination of acetate and gluconate may be used.

In another embodiment, an aqueous red blood cell storage medium is provided that may include about 3 to 90 mM of sodium citrate; 15 to 40 mM of sodium phosphate; 20 to 140 mM of glucose; 20 to 100 mM of mannitol and 1 to 2.5 mM of adenine. The storage solution may have a pH of from about 8.0 to about 8.8, and more preferably, about 8.4. The osmolarity may be in the range of about 150 to 350 mOsm $L^{-1}$ and more preferably, about 314 mOsm $L^{-1}$.

In one example, the "E-Sol 5" storage medium identified in the Table 1, above, is an aqueous solution that is constituted from a dextrose (i.e. glucose) solution that, at approximately 25° C. has a generally acidic pH in the range of 3.5 to 5.5 and more particularly a pH of 3.7 to 5.3, and even more preferably about 4.0, and a second solution that includes sodium phosphate, mannitol and adenine that has a generally basic pH in the range of 8.0 to 9.0. Once the two solutions are combined, the final E-Sol 5 composition includes the following components indicated, in the range of 3 to 90 mM of sodium citrate; 15 to 40 mM of sodium phosphate; 20 to 140 mM of glucose; 20 to 100 mM of mannitol and 1 to 2.5 mM of adenine, and more particularly, the components indicated in the amount shown in Table 1, above.

By way of example, but not limitation, illustrations of methods and systems for providing red blood cell products with reduced plasma as described herein are provided below:

Example 1

In this example, whole blood was processed using several different procedures to produce a red blood cell product. The red blood cell product produced by each procedure was stored for up to 42 days in the E-Sol 4 additive solution and cell properties were assayed at 7 day intervals.

FIG. 7 is a graph showing extracellular 2,3-DPG concentrations for over time for the red blood cell products made by each procedure. Table 2 provides a key to the legend of FIG. 7.

TABLE 2

| Sample | Procedure | % Plasma Content in Supernatant |
|---|---|---|
| A | Treat/Spin | 7 |
| B | Storage in excess additive solution | 11 |
| C | Alternate buffy coat | 11 |
| D | OptiPressII | 15 |
| E | Alyx Standard | 29 |

For sample A in FIG. 7, 500 mls of whole blood was collected in a bag (Fenwal 4R1590 blood packs) and subjected to spin (5000 g) to separate plasma and red blood cells. Plasma was expressed from the bag by manual pressing. Approximately 220 mls of E-Sol 4 was transferred to the red blood cell concentrate and mixed forming an intermediate solution. The bag was centrifuged and the supernatant of plasma-containing solution expressed. 110 mls of E-Sol 4 was added to the concentrated red blood cells and the cells were stored and samples taken at seven day intervals for biochemical assays. The plasma content at each step of the procedure was determined as follows:

Calculation of Initial Plasma Volume $$Volume_{WB}(mL) = \frac{Weight_{BPU+WB}(g) - \text{Tare } Weight_{BPU}(g) - 70 \text{ g } CPD}{\frac{Hct}{100} \times 1.09\frac{g}{mL} + \left(1 - \frac{Hct}{100}\right) \times 1.03\frac{g}{mL}}$$

$[(Volume)] \downarrow (\text{initial plasma})(mL) = [(Volume)] \downarrow WB(mL) \times (1 - Hct/100)$ Calculation of Plasma Volume after $1^{st}$ Expression $$Volume_{expressed\ plasma}(mL) = \frac{Weight_{Bag5+plasma}(g) - \text{Tare } Weight_{Bag5}(g)}{1.03\frac{g}{mL}}$$

$Volume_{plasma\ remaining}(mL) =$
$\quad Volume_{initial\ plasma}(mL) - Volume_{expressed\ plasma}(mL)$ Calculation of % Plasma in Supernatant After Addition of E-Sol 4

$$Volume_{AS\ added}(mL) = \frac{Weight_{Bag3+AS}(g) - \text{Tare } Weight_{Bag3}(g)}{1.01\frac{g}{mL}}$$

$$\%\ Plasma_{supernatant} = \frac{Volume_{plasma\ remaining}(mL)}{Volume_{plasma\ remaining}(mL) + Volume_{AS\ added}(mL)} \times 100\%$$

Calculation of Plasma Volume Remaining After $2^{nd}$ Expression $Volume_{plasma-AS\ expressed}(mL) =$ $$\frac{Weight_{Bag3+\frac{plasma}{AS}}(g) - \text{Tare } Weight_{Bag3}(g)}{\frac{\%\ plasma}{100} \times 1.03\frac{g}{mL} + \left(1 - \frac{\%\ plasma}{100}\right) \times 1.01\frac{g}{mL}}$$

$Volume_{plasma-AS\ remaining}(mL) = Volume_{plasma\ remaining}(mL) +$
$\quad Volume_{AS\ added}(mL) - Volume_{plasma-AS\ expressed}(mL)$ $Volume_{residual\ plasma}(mL) =$
$\quad Volume_{plasma-AS\ remaining}(mL) \times \%\ Plasma_{supernatant}$ For sample B, a red blood cell concentrate was prepared from one unit of whole blood using a standard procedure for the Fenwal Alyx device as generally shown in FIGS. 3 and 4. An excess of additive solution, 330 mls of E-Sol 4, was mixed with the red blood cell concentrate in a bag and the preparation stored. In this case, the hematocrit during storage was approximately 30%. Samples for biochemical assays taken at 7 day intervals.

For sample C, a red blood cell product was prepared using a system similar to that shown in FIG. 6. Whole blood was subjected to centrifugation (5000 g for 10 min.) and the plasma expressed into an additional container. In addition, approximately 25 mls of red blood cells was expressed into a third container. 130 mls of E-sol 4 was added to the concentrated red blood cells and the cells were stored and samples taken at seven day intervals for biochemical assays. The results of the measured values for individual samples for 2,3-DPG values are summarized in Table 3. The data are also summarized in FIG. 7.

TABLE 3

| | Concentration of 2,3-DPG (µmol/ml) | | | | | | |
|---|---|---|---|---|---|---|---|
| Sample | 0 | 7 | 14 | 21 | 28 | 35 | 42 |
| A | 2.5 | 3.3 | 3.6 | 1.5 | 1.0 | 0.6 | 0.4 |
| B | 1.8 | 2.4 | 2.7 | 2.3 | 1.9 | 1.6 | 1.2 |
| C | 2.2 | 2.5 | 2.9 | 1.9 | 1.6 | 1.0 | 0.8 |
| D | 2.4 | 3.3 | 3.5 | 2.6 | 1.9 | 1.3 | 1.0 |
| E | 2.1 | 2.7 | 2.5 | 1.1 | 1.3 | 0.4 | 0.2 |

For sample D, whole blood was subjected to a hard spin (5000 g for 10 min.) and plasma and a buffy coat layer were expressed using an Opti-Press II. Approximately 110 mls of E-Sol 4 was added to the concentrated red blood cells and the cells were stored and assayed for various biochemical parameters at 7 day intervals.

For sample E, a concentrated red blood cell sample was prepared using a standard Alyx procedure from one unit of blood without further treatment with additive solution. Thus, this procedure serves as a control for Sample B.

Example 2

Fifteen whole blood (WB) units (500 mL±10%) were collected into 4R1590 blood packs (Fenwal) and stored for 1-4 hours at room temperature before separation (5000×g, 10 min). In twelve WB units, the plasma was expressed and the concentrated RBCs were washed with E-Sol 4 (220 mL) and separated again (5000×g, 10 min). E-Sol 4 (110 mls) was added to the RBC concentrate and subsequently leukofiltered (test). In the three remaining WB units, 110 mL of Adsol (a chloride containing additive solution used as a control) was added to each and then leukofiltered. The RBC concentrates were stored for 42 days with weekly sampling of in vitro parameters. Summary data collected at day 0, 14, 21, and 42 are given in the table below (mean±SD). Residual plasma was 9.8±0.9 m: in test and 33.8±1.3 mL in control units. Extracellular pH (22° C.) and K$^+$ (mmol/L) were similar at Day 42 for test and control—(6.22±0.06 vs. 6.24±0.01) and (56.8±2.4 vs. 56.6±3.9), respectively. Glucose (mmol/L) was present throughout storage for test and control units (17.3±1.8 and 36.2±3.1, at Day 42, respectively). Lactate concentration (mmol/L) was higher in test units at Day 42 (37.6±2.5 vs. 31.8±1.8).

The results (table 4) show that at Day 42, RBCs stored with minimal residual plasma and E-Sol 4 show lower % hemolysis than non-washed controls. Notably, 2,3-DPG levels are at or above Day 0 levels for 21 days and ATP is maintained above 80% of Day 0 throughout 42-day storage.

TABLE 4

| | | Day 0 | Day 14 | Day 21 | Day 42 |
|---|---|---|---|---|---|
| % Hemolysis | Test | 0.08 ± 0.01 | 0.12 ± 0.01 | 0.12 ± 0.01 | 0.16 ± 0.02 |
| | Control | 0.04 ± 0.01 | 0.08 ± 0.01 | 0.11 ± 0.02 | 0.23 ± 0.08 |
| ATP, µmol/g Hb | Test | 4.2 ± 0.4 | 5.2 ± 0.5 | 4.9 ± 0.5 | 3.3 ± 0.4 |
| | Control | 4.8 ± 0.5 | 5.0 ± 0.2 | 4.3 ± 0.9 | 3.0 ± 0.3 |
| 2,3 DPG, µmol/g Hb | Test | 14.4 ± 1.6 | 20.4 ± 2.1 | 14.4 ± 1.9 | 2.3 ± 1.0 |
| | Control | 13.0 ± 2.0 | 4.1 ± 6.3 | 2.7 ± 2.3 | 0.3 ± 0.3 |

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. An automated method for obtaining a readily transfusible volume of a plasma-reduced red blood cell product wherein said plasma comprises 15% or less of a supernatant component of said red blood cell product, said method comprising:
   a) separating in a separation chamber of a centrifugal separation device a volume of anticoagulated blood into concentrated red blood cells and a supernatant component consisting essentially of a residual amount of plasma and anticoagulant;
   b) determining an initial plasma volume in said separated supernatant;
   c) removing an amount of said supernatant component to provide a red blood cell concentrate and remaining supernatant;
   d) determining the volume of plasma remaining in said supernatant after said removing step;
   e) introducing said red blood cell concentrate into a container in flow communication with said separation chamber;
   f) combining a portion of said red blood cell concentrate with a selected amount of additive solution wherein said
   amount of additive solution suitable for long term storage of red blood cells to be added to said red blood cell concentrate portion is selected such that the percentage of plasma in a final red blood cell product, by volume, is 15% or less of said supernatant wherein said supernatant consists essentially of plasma, anticoagulant and additive solution;
   introducing said combined red blood cell concentrate portion and additive into said separation chamber;
   g) separating said red blood cell concentrate from a supernatant component consisting essentially of plasma, anticoagulant and additive solution; and h) collecting said red blood cell concentrate to arrive at said final red blood cell product.

2. The method of claim 1 comprising adding an amount of additive solution so that the percentage of plasma, by volume, of said supernatant consisting essentially of plasma, anticoagulant and additive solution is between about 6% and 11%.

3. The method of claim 1 comprising storing said red cell product for up to 42 days of storage.

4. The method of claim 3 further comprising storing said final red blood cell product in said additive solution for at least 28 days wherein 2, 3-DPG levels of the red blood cells in said final red blood cell product are maintained to at least 50% after said 28 days of storage relative to 2-3-DPG levels of said red blood cell product at the time of step (f).

5. The method of claim 1 wherein said anticoagulated blood comprises anticoagulated whole blood.

6. The method of claim 1 wherein said anticoagulated blood comprises concentrated red blood cells that have been separated from anticoagulated whole blood.

7. The method of claim 1 wherein said additive solution comprises about 20 to about 140 mM of glucose, about 20 to about 100 mM mannitol, about 15 to about 40 mM sodium phosphate dibasic, about 3 to about 90 mM sodium citrate and about 1 to 2.5 mM adenine, said additive solution being chloride-free and having a pH of between 8.0 and 9.0.

8. The method of claim 1 comprising:
a) separating about 400-500 ml of anticoagulated whole blood to provide about 150-250 ml of concentrated red blood cells and a supernatant component comprising at least one of plasma and anticoagulant;
b) removing by centrifugation substantially all of said supernatant to provide an initial red blood cell concentrate volume of about 150-250 ml and about 10-30 ml of remaining supernatant;
c) combining said initial red blood cell concentrate with about 100-300 ml of said chloride-free, additive solution to provide an intermediate red blood cell product;
d) separating by centrifugation said intermediate red blood cell product to provide about 150-250 ml of concentrated red blood cells and a supernatant component comprising at least plasma, anticoagulant and said additive solution;
e) removing substantially all of said supernatant component from said intermediate red blood cell product to provide a treated red blood cell concentrate comprising about 150-250 ml of red blood cells and about 10-30 ml of remaining supernatant; and
f) combining said treated red blood cell concentrate with about 100-150 ml of said chloride-free, additive solution to provide a final red blood cell product wherein the percentage of plasma in said supernatant component is no greater than 15%.

9. The method of claim 1 further comprising:
(a) combining said red cell concentrate and remaining supernatant with an amount of additive solution after step (c) of claim 1 to arrive at an intermediate red cell product;
(b) further separating said intermediate red blood cell product into a red blood cell concentrate and a supernatant component comprising plasma, anticoagulant and additive solution; and
(c) removing an amount of said supernatant component to provide a red blood cell concentrate and remaining supernatant from said intermediate red blood cell product.

10. The method of claim 1 comprising determining the initial amount of plasma present in a quantity of blood without anticoagulant.

11. The method of claim 1 comprising determining the initial amount of plasma in said quantity of blood by determining the hematocrit of the blood prior to anticoagulation and determining the amount of anticoagulant in said anticoagulated blood.

12. The method of claim 1 comprising introducing said blood into said device further including a controller configured to determine the amount of plasma remaining in the supernatant.

13. The method of claim 12 wherein said controller is configured to determine the selected amount of additive solution required to arrive at an amount of plasma that as a percentage of plasma, anticoagulant and additive solution is 15% or less, said method further comprising determining whether or not the amount of additive solution required exceeds a pre-selected amount.

14. The method of claim 13 wherein said controller is configured to effect said combining of said determined amount of said additive solution with said initial red blood cell concentrate and said residual plasma.

15. The method of claim 9 further comprising determining said amount of plasma remaining in the supernatant of said final red blood cell product.

16. The method of claim 1 further comprising transfusing said red blood cell product obtained in step (h).

17. The method of claim 9 further comprising leukoreducing said final red blood cell product.

18. The method of claim 9 comprising combining said red cell concentrate and remaining supernatant with said amount of additive in said separation chamber of said centrifugal separation device.

* * * * *